United States Patent [19]

Beebe

[11] Patent Number: 4,499,548
[45] Date of Patent: Feb. 12, 1985

[54] DATA COMPRESSION APPARATUS

[75] Inventor: Richard P. Beebe, Billerica, Mass.

[73] Assignee: Hewlett-Packard Company, Palo Alto, Calif.

[21] Appl. No.: 433,748

[22] Filed: Oct. 12, 1982

Related U.S. Application Data

[63] Continuation of Ser. No. 165,169, Jul. 2, 1980, abandoned, and Ser. No. 165,172, Jul. 2, 1980.

[51] Int. Cl.³ .............................................. H03K 5/20
[52] U.S. Cl. ...................................... 364/575; 382/56; 328/151
[58] Field of Search ................ 364/575, 900; 328/151, 328/135; 358/260, 138; 340/722, 728, 747; 382/52, 54, 56

[56]  References Cited

U.S. PATENT DOCUMENTS

| | | | |
|---|---|---|---|
| 3,694,581 | 9/1972 | Fletcher et al. | 179/15.55 R |
| 3,707,680 | 12/1972 | Gabbard et al. | 179/15.55 R |
| 4,053,840 | 10/1977 | Baron | 179/15.55 R |
| 4,137,568 | 1/1979 | Dlugos | 364/575 |
| 4,183,087 | 1/1980 | Huelsman | 358/138 |
| 4,223,681 | 9/1980 | Sherman | 364/575 |

Primary Examiner—Gary Chin
Attorney, Agent, or Firm—Donald N. Timbie

[57]  ABSTRACT

Apparatus that selects for display that data sample of each exclusive and successive group of data samples which differs the most in amplitude from the average amplitude of the previous group of data samples and apparatus that selects for display that data sample of each exclusive and successive group of data samples which differs the most in amplitude from the data sample selected for display from the previous group.

4 Claims, 22 Drawing Figures

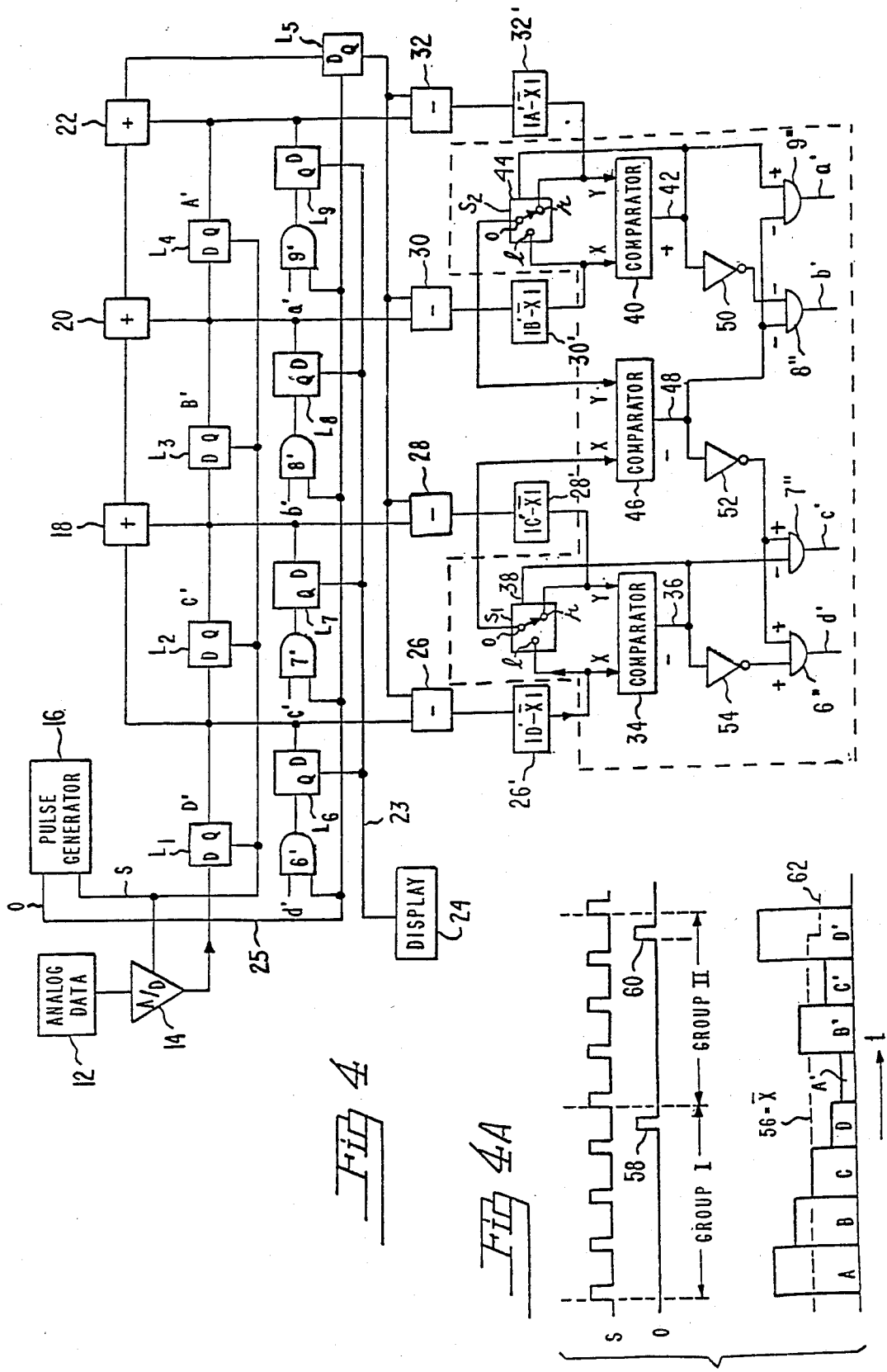

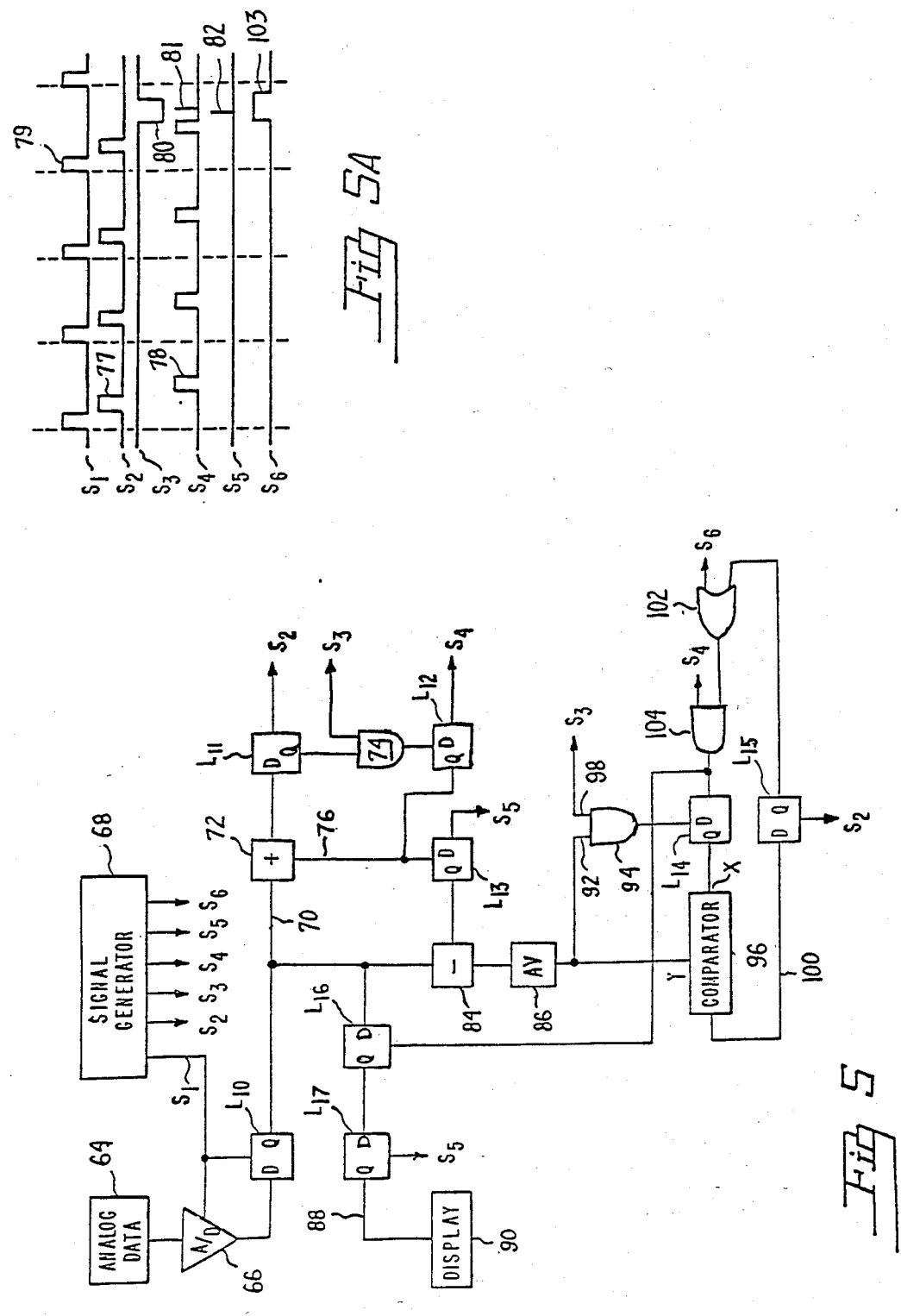

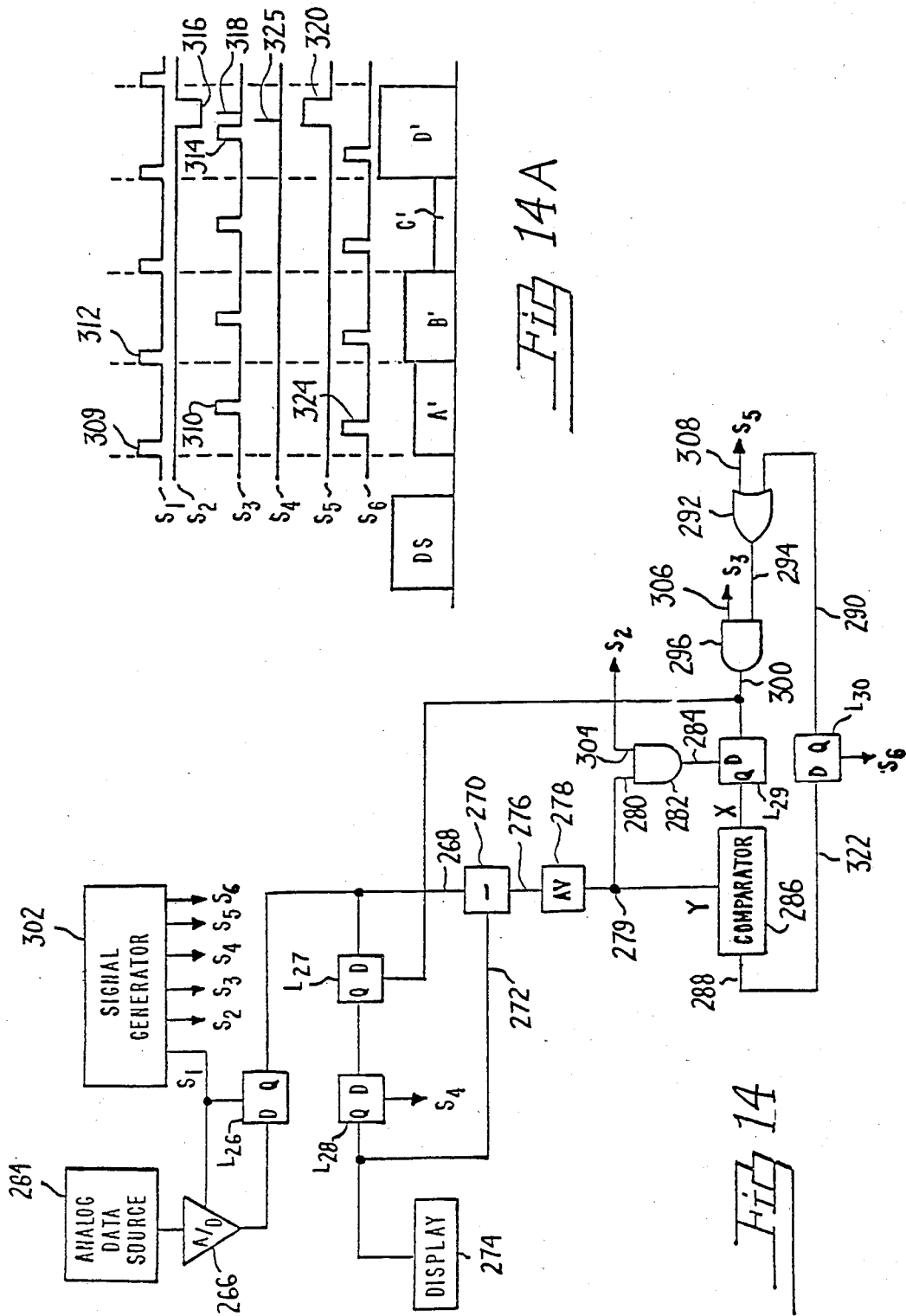

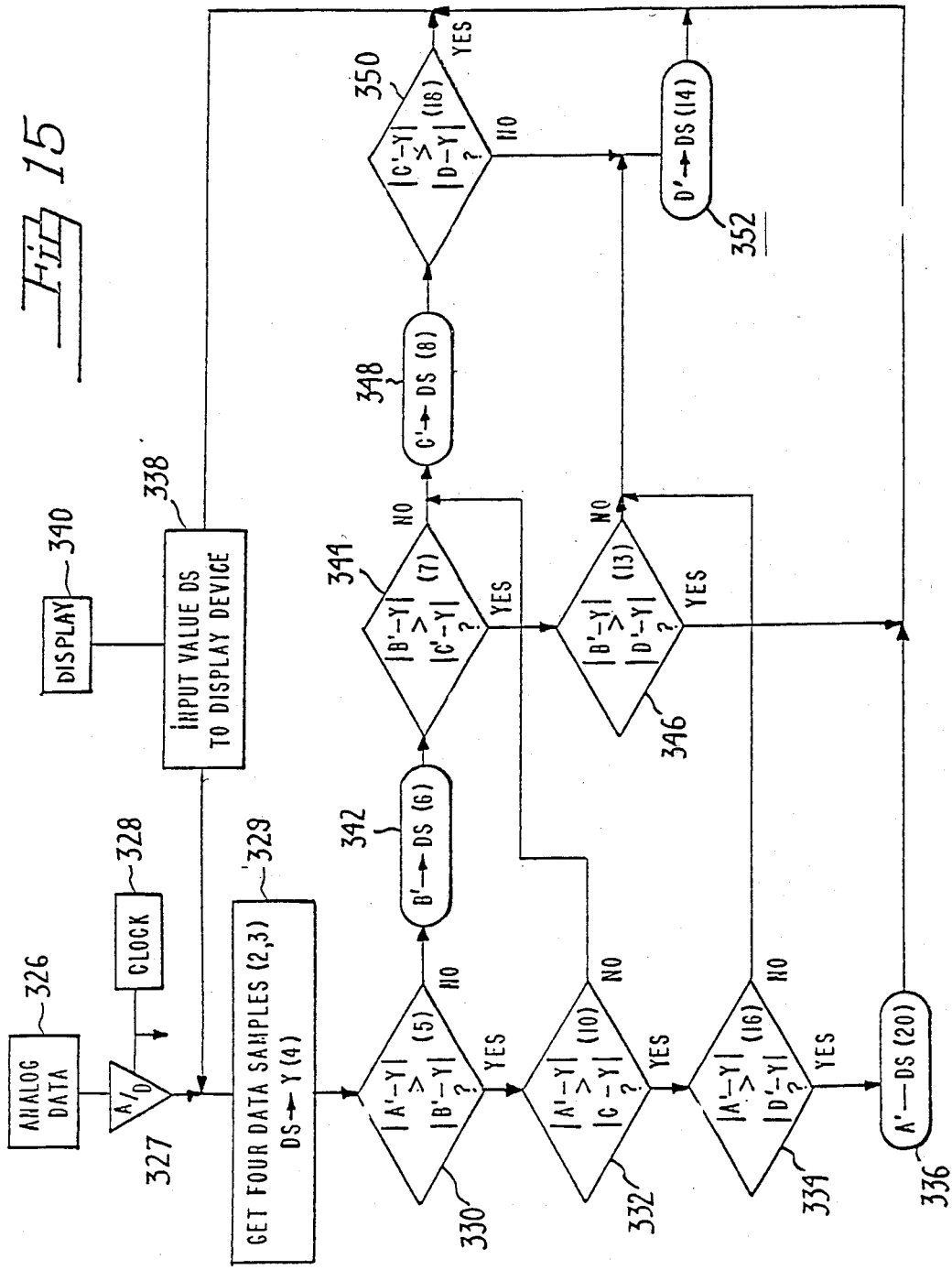

DATA COMPRESSION APPARATUS

This application is a continuation of U.S. patent application Ser. No. 165,169 abandoned, filed July 2, 1980, and U.S. patent application Ser. No. 165,172, filed July 2, 1980.

BACKGROUND OF THE INVENTION

Equipment for monitoring physiological functions, such as the electrical activity of the heart, often outputs digital data samples at a rate that is greater than economical cathode ray tube display or other monitoring apparatus can accommodate. For example, the digital data samples may occur every two milliseconds and the display apparatus may only be capable of displaying a sample every eight milliseconds, thus requiring a four-to-one data compression. One way of providing the required compression of the data in this situation would be to average each successive group of four data samples. Unfortunately, however, this reduces the amplitude of narrow pace pulses that are of utmost importance to a point where they may become indistinguishable from noise.

BRIEF DESCRIPTION OF THE INVENTION

In accordance with a first invented procedure, the absolute difference between the value of each data sample in a group of data samples and the average value of the previous group of data samples is determined and that data sample which has the largest absolute difference is selected as the display sample. The data samples are supplied to an input to which means are coupled for deriving a representation of the average value of the data samples in each group, means are provided for deriving the absolute difference between the value of each sample of the next group of data samples and the average value for the previous group, and means are provided for making that data sample for which the absolute difference is greatest available as a display sample for the display or other monitoring apparatus. The number of samples in a group equals the data compression required.

In accordance with a second invented procedure, the data sample of each group that is selected as a display sample is that data sample which differs the most from the data sample that was selected as the display sample in the previous group. Apparatus for performing this function is comprised of an input to which data samples may be applied, an output that may be coupled to a display means, means for conducting to said output the data sample of each successive group of samples having a value that is farthest from the value of the data sample selected from a previous group.

BRIEF DESCRIPTION OF THE DRAWINGS

FIG. 4 is a block diagram of a circuit that selects data samples to be used as display samples in accordance with the first invented procedure in which the absolute differences between all data samples of a group and the average of the data samples of the previous group are made simultaneously available before the data sample having the largest absolute difference is selected as the display sample;

FIG. 4A illustrates signals used in controlling the operation of the circuit of FIG. 4;

FIG. 5 is a block diagram of a circuit that selects data samples to be used as display samples in accordance with the first invented procedure in which the absolute differences between each data sample of one group and the average of the data samples of the previous group are made successively available and successively compared before selecting the data sample having the largest absolute difference as the display sample;

FIG. 5A illustrates signals used in controlling the operation of the circuit of FIG. 5;

FIG. 14 is a block diagram of another circuit for selecting data samples to be used as display samples in accordance with the second invented procedure in which the absolute differences between each data sample of one group and the display sample previously selected from the previous group are made successively available and successively compared before selecting the data sample having the largest absolute difference as the display sample;

FIG. 14A illustrates certain control pulses used in FIG. 14;

FIG. 15 is a flow chart that is a basis for a program for a computer or processor that can select the data samples in accordance with the second invented procedure;

DETAILED DESCRIPTION OF THE INVENTION

In the following detailed descriptions of embodiments of this invention, the terms "data sample" and "display sample" will refer to the actual values.

Figure 1:
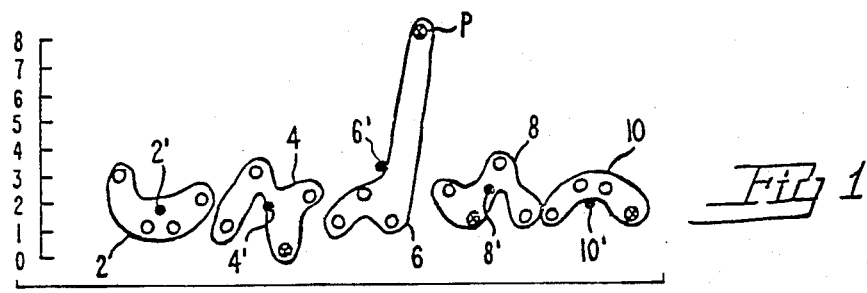
FIG. 1 illustrates a number of typical data samples from which an electrocardiogram can be formed and the average value of each group of four.
Figure 2:
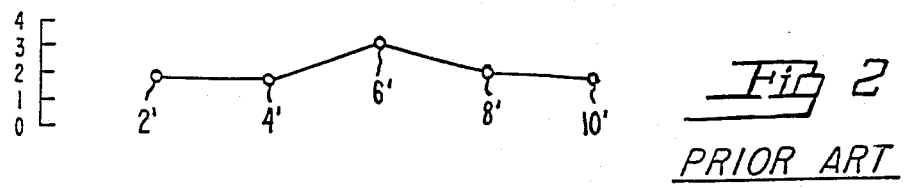
FIG. 2 illustrates the display samples that would be produced from the data samples of FIG. 1 if each display sample is the average value of each exclusive group of four data samples.

In FIG. 1, each data sample is indicated by an "O", successive exclusive groups of four data samples are respectively encircled by separate lines 2, 4, 6, 8 and 10, and the average of the data samples in each group are indicated by points 2', 4', 6', 8' and 10' respectively. The data point P in the group 6 represents a pace pulse. FIG. 2 illustrates the electrocardiogram that would result if the data is compressed by using the average value of each group of four data samples, i.e., points 2', 4', 6', 8' and 10', as the display samples. Note that the pace pulse P is represented by the display sample 6' of thr group 6 and is greatly attenuated.

Figure 3:
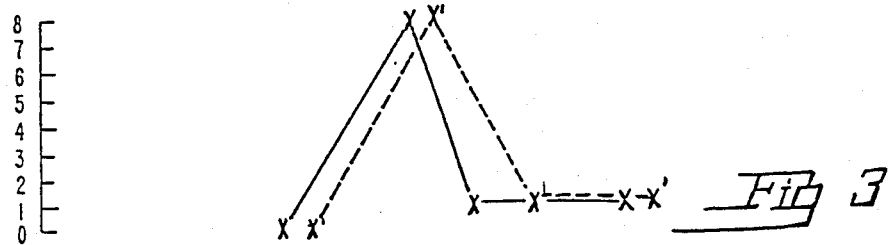
FIG. 3 illustrates the data samples of FIG. 1 that would be selected as display samples in accordance with a first invented procedure.

In accordance with this invention, one data sample in each of the groups 2, 4, 6, 8 and 10 is selected as a display sample. In accordance with a first invented procedure, this is the data sample that differs from the average of the previous group of data samples by the greatest absolute amount. In FIG. 1, the data samples that are selected as display samples in accordance with this procedure are indicated by an "X" within the "O". They are separately plotted in FIG. 3 and joined by a solid line. It can be seen that the pace pulse P is selected as a display sample. In view of the fact that the data sample of a group that is to be the display sample cannot be selected until all data samples of the group have been examined, the data sample that has been selected as a display sample is supplied to the display means at a time between the last data sample of one group and the first data sample of the next, as indicated by the X's in FIG. 3 that are joined by a dashed line.

Reference is now made to the circuit of FIG. 4 that selects the data samples of each group of four that are to be the display samples in accordance with the first invented procedure. The means for deriving the average value of each group of data samples is as follows. Analog data, such as the output of an ECG machine, is supplied from a source 12 to an analog-to-digital converter 14 that provides digitized data samples at its output at a rate and duration determined by the triggering pulses S of FIG. 4A. The triggering pulses S are provided by a pulse generator 16, which may be a digital counter. The digitized data samples at the output of the A/D converter 14 are loaded in a latch $L_1$ that is connected in series with latches $L_2$, $L_3$ and $L_4$. The Q output of each of these latches is connected to the D input of the next latch in the series so as to form a shift register, and all the latches are strobed at the same time by the pulses S. The inputs of an adder 18 are respectively connected to the Q outputs of the latches $L_1$ and $L_2$; the inputs of an adder 20 are respectively connected to the output of the adder 18 and the Q output of the latch $L_3$; and the inputs of an adder 22 are respectively connected to the output of the adder 20 and the Q output of the latch $L_4$. The output of the adder 22, except for the two least significant bits, is connected to the D input of a latch $L_5$ so as to divide the output of the adder 22 by four. Thus, after four triggering pulses of a first group I of FIG. 4A, the successive data samples A, B, C and D of that group are at the outputs of the latches $L_4$, $L_3$, $L_2$ and $L_1$ respectively, and their sum appears at the output of the adder 22. One-fourth of this sum, or the average of the data samples A, B, C and D, is loaded into the D input of the latch $L_5$ by applying all but the two least significant bits to the D input. This average value is transferred to the Q output of the latch $L_5$ by a pulse O, FIG. 4A, that is provided by the pulse generator 16. Inasmuch as the pulses O occur between the last pulse S of a group and the first pulse S of the next group, the average value appearing at the Q output of the latch $L_5$ during the group II is the average value of the data samples of the group I.

Transfer of a data sample selected in a manner to be described to a display sample output bus 23 and a display means 24 is accomplished as follows. The data samples at the Q outputs of the latches $L_1$, $L_2$, $L_3$ and $L_4$ are also respectively present at the D inputs of the latches $L_6$, $L_7$, $L_8$ and $L_9$ by virtue of connected therebetween, and all the Q outputs of the latches $L_6$, $L_7$, $L_8$ and $L_9$ are connected to the display sample output bus 23. The outputs of AND gates 6', 7', 8' and 9' are respectively connected to the trigger inputs of the latches $L_6$, $L_7$, $L_8$ and $L_9$, and one input of each AND gate is connected by a bus 25 to the output of the pulse generator 16 at which the pulses O of FIG. 4A appear. In a manner to be explained, one of the other inputs d', c', b' and a' of the respective AND gates 6', 7', 8' and 9' is made to have a high state during a pulse O so that the output of that AND gate will become high and trigger the latch to which it is connected. The data sample at the input of that latch is the display sample and is transferred to the Q output and via the display sample output bus 23 to the display means 24.

Derivation of the absolute values of the differences between each data sample of one group and the average value of the data samples of the previous group is performed by the following parts of the circuit. One set of inputs of subtractors 26, 28, 30 and 32 are respectively connected to the Q outputs of the latches $L_1$, $L_2$, $L_3$ and $L_4$ at which the data samples appear, and the other inputs of these subtractors are connected to the Q output of the latch $L_5$ at which the average value of the previous group of data samples appears. Thus, when the data samples D', C', B' and A' of group II are respectively at the Q outputs of $L_1$, $L_2$, $L_3$ and $L_4$, the differences between these data samples and the average value of the data samples of group I respectively appear at the outputs of the subtractors 26, 28, 30 and 32. The absolute values of these differences, $|D'-\overline{X}|$, $|C'-\overline{X}|$, $|B'-\overline{X}|$ and $|A'-\overline{X}|$ are respectively derived by absolute value circuits 26', 28', 30' and 32' that are connected to the outputs of the subtractors 26, 28, 30 and 32 respectively.

The selection of the data sample of a group causing the largest absolute difference is performed by the following circuit components. The output of the absolute value circuit 26' is connected to the X input of a comparator 34 as well as to an input terminal l of a switch $S_1$, and the output of the absolute value circuit 28' is connected to the Y input of the comparator 34 as well as to an input terminal r of the switch $S_1$. The output 36 of the comparator 34 is connected to a control terminal 38 of the switch $S_1$. When the value at the input X of the comparator 34 is less than the value at its Y input, the output 36 is in a high state and the output O of the switch $S_1$ is connected to the input terminal r.

The output of the absolute value circuit 30 is connected to the X input of a comparator 40 as well as to an input terminal 1 of a switch $S_2$, and the output of the absolute value circuit $32'$ is connected to the Y input of the comparator 40 as well as to an input terminal r of the switch $S_2$. The output 42 of the comparator 40 is connected to a control terminal 44 of the switch $S_2$. When the value at the input X of the comparator 40 is less than the value at its Y input, the output 42 is in a high state and the output O of the switch $S_2$ is connected to the input terminal r. The outputs O of the switches $S_1$ and $S_2$ are respectively connected to the X and Y inputs of a comparator 46 which has an output 48. As is the case with the other comparators, the output 48 is in a high state if the value at the input X is less than the value at the input Y.

The logic circuits now to be described operate in response to the outputs of the comparator 34, 40 and 46 to raise the state of one of the respective inputs $a'$, $b'$, $c'$ or $d'$ of the AND gates $9'$, $8'$, $7'$ and $6'$ so that it will trigger the associated latch and cause it to transfer the data sample at its input to the data sample output bus 24 when the output strobing pulse O occurs. This data sample is then the display sample. The output of AND gates $9''$, $8''$, $7''$ and $6''$ are respectively connected to the inputs $a'$, $b'$, $c'$ and $d'$ of the AND gate $9'$, $8'$, $7'$ and $6'$. The inputs of the AND gate $9''$ are respectively connected to the outputs 42 and 48 of the comparators 40 and 46; the inputs of AND gate $8''$ are respectively connected to the output 48 of the comparator 46 and to the output 42 of the comparator 40 via an inverter 50; the inputs of the AND gate $7''$ are respectively connected to the output 36 of the comparator 34 and via an inverter 52 to the output 48 of the comparator 46; and the inputs of the AND gate $6''$ are respectively connected to the output 36 of the comparator 34 via an inverter 54 and via the inverter 52 to the output 48 of the comparator 46.

Operation of FIG. 4

The operation of the circuit of FIG. 4 for the purpose of selecting a sample from Group II will now be explained by reference to the graphs of FIG. 4A. Assume that the values of the data samples occurring during consecutive exclusive groups of samples I and II are respectively in the order A, B, C, and D and $A'$, $B'$, $C'$ and $D'$ as illustrated in FIG. 4A. After the fourth data sample D of Group I has been received, the data samples A, B, C and D are respectively at the outputs of the latches $L_4$, $L_3$, $L_2$ and $L_1$, and the output of the adder 22 is the sum of A, B, C and D. Because the two least significant bits of this sum are not conducted to the D input of the latch $L_5$, the value at its D input is the average of the data samples of Group I or $(A+B+C+D)/4$ that is indicated by the dashed line 56. This is the condition that prevails when an output strobing pulse 58 of Group I occurs. The output strobing pulse 58 triggers the latch $L_5$, causing the average value at its D input to be transferred to its Q output and thus at one input of each of the subtractors 26, 28, 30 and 32. This average value remains at the Q output of the latch $L_5$ during the reception of the next group II of data samples $A'$, $B'$, $C'$ and $D'$ and until the output strobing pulse 60 of the group II occurs.

After the data samples $A'$, $B'$, $C'$ and $D'$ of the group II have arrived and just prior to the occurrence of the output strobing pulse 60, the values at the outputs of the latches $L_4$, $L_3$, $L_2$ and $L_1$ are $A'$, $B'$, $C'$ and $D'$ respectively as indicated on the drawing. These values are respectively applied to inputs of the subtractors 32, 30, 28 and 26, and the average value $\overline{X}=(A+B+C+D)/4$ of the data samples of group I, as represented by the dashed line 56 of FIG. 5A, is applied to the other inputs from the Q output of the latch $L_5$ so that the outputs of the subtractors are respectively $A'-\overline{X}$, $B'-\overline{X}$, $C'-\overline{X}$ and $D'-\overline{X}$. The absolute values $|A'-\overline{X}|$ and $|B'-\overline{X}|$ are derived by the absolute value circuits $32'$ and $30'$ and are respectively applied to the Y and X inputs of the comparator 40. Since, in accordance with the data samples illustrated in FIG. 4A, $|A'-\overline{X}| > |B'-\overline{X}|$, the output of the comparator 40 will be in a high state as indicated and the output O of the switch $S_2$ will be connected to the input terminal R so as to conduct the value $|A'-\overline{X}|$ to the Y input of the comparator 46.

The outputs of the subtractors 26 and 28 are respectively $D'=\overline{X}$ and $C'-\overline{X}$, and their absolute value $|D'-\overline{X}|$ and $|C'-\overline{X}|$ are derived by the absolute value circuits $26'$ and $28'$ and respectively applied to the X and Y inputs of the comparator 34. Inasmuch as $|D'-\overline{X}| > |C'-\overline{X}|$, the output 36 of the comparator 34 is low as indicated so as to cause the output O of the switch $S_1$ to be connected to the input terminal L and thereby conduct the value $|D'-\overline{X}|$ to the X input of the comparator 46. In this example, the value $|A'-\overline{X}|$ is greater than the value $|B'-\overline{X}|$ so that the output of the comparator 46 is low as indicated.

With the states indicated at the outputs 36, 48 and 42 of the comparators 34, 46 and 40 being (−), (−) and (+) respectively, the states applied to the inputs of the AND gates $6''$, $7''$, $8''$ and $9''$ will be as indicated so that the output of the AND gate $6'$, which is connected to the input $d'$ of the AND gate $6'$, is the only one that has a high state. This enables the latch $L_6$ to transfer the value of the data sample $D'$ from its D input to its Q output when the output data strobing pulse 60 occurs. At the same time, the average value (indicated by the dashed line 62) of the data samples $A'$, $B'$, $C'$ and $D'$ that is present at the D input of the latch $L_5$ is transferred to the Q output so as to be ready for comparison with the data samples of the next group, not shown.

Alternative Circuit

In the circuit of FIG. 4 just described, the absolute differences between each data sample of one group and the average of the values of the data samples of the previous group were made simultaneously available and compared at one time. In the circuit of FIG. 5, the absolute differences between the data samples of one group and the average of the data samples of the next previous group are made available in sequence and are compared successively so as to determine the absolute difference.

Turning now to the details of FIG. 5, it is seen that the analog signals are supplied by a source 64 to an A/D converter 66 having its output coupled to the D input of a latch $L_{10}$. In the interest of simplicity, only one digital data line is shown, but as many as required can be used. A signal generator 68 supplies timing pulses $s_1$, $s_2$, $s_3$, $s_4$, $s_5$ and $s_6$ as illustrated in FIG. 5A. The broad pulses of each of the signals $s_1$, $s_2$, $s_3$, $s_4$, $s_5$ and $s_6$ could be provided by connecting the inputs of an OR gate to appropriate outputs of a Johnson counter, and the narrow pulses could be provided by connecting an astable multivibrator at a selected output of the counter. The signal $s_1$ is applied to the A/D converter 66 and to the latch $L_{10}$.

The Q output of the latch $L_{10}$ is coupled to the following means for deriving the average value of the data samples in each group. One input 70 of an adder 72 is connected to the Q output of the latch $L_{10}$, and the output of the adder 72 is connected to the D input of a latch $L_{11}$. A signal $s_2$ from the signal generator 68 is applied to the trigger input of the latch $L_{11}$, and the Q output of the latch $L_{11}$ is connected to one input of an AND gate 74. Only one AND gate 74 is shown, but there would be as many as there are data lines. A signal $s_3$ is applied to the other input of the AND gate 74, and its output is connected to the D input of a latch $L_{12}$. A signal $s_4$ is applied to the trigger input of the latch $L_{12}$, and its Q output is connected to the other input 76 of the adder 72 as well as to the D input of a latch $L_{13}$.

Operation of the data sample averaging means is as follows. Assume that the latch $L_{12}$ has been cleared so that its Q output is zero when the first data sample of a group of samples arrives at the input 70 of the adder 72 in response to the application of a pulse of the signal $s_1$ to the latch $L_{10}$. The output of the adder 72 then equals the value of the first data sample and is connected to the D input of the latch $L_{11}$. Before the next pulse of the signal $s_1$ occurs, a pulse such as 77 of the signal $s_2$ triggers the latch $L_{11}$ so as to transfer the value of the first data sample at its D input to its Q output and thus to one input of the AND gate 74. Because the signal $s_3$ that is applied to the other input of the AND gate 74 is in a high state during the entire time that samples of a group are received, the first data sample passes through the adder to the D input of the latch $L_{12}$. This data sample is then transferred to the Q output of the latch $L_{12}$ and therefore to the input 76 of the adder 72 when the latch $L_{12}$ is triggered by a subsequent pulse 78 in the signal $s_4$. As seen in FIG. 5A, the latter occurs between a pulse in the signal $s_2$ and the time when the next pulse of the signal $s_1$ occurs. When the second data sample arrives at the input 70 of the adder 72 in response to the next pulse in the signal $s_1$, it is added to the first data sample that has been applied to the input 76 of the adder 72 from the Q output of the latch $L_{12}$. The output of the adder 72 now has a value equal to the sum of the first and second data samples. Thus, after the last data sample of a group of four samples is received, a value equal to their sum appears at the Q output of the latch $L_{12}$. All but the two least significant bits of the sum value are passed to the D input of the latch $L_{13}$ so that the value at its D input is the average value of the four data samples of the group.

After each group of data samples, the Q output of the latch $L_{12}$ is set to zero and the average value is retained at the Q output of the latch $L_{13}$ for comparison with the data samples of the next group in the following manner. After the last pulse 79 for a group occurs in the signal $s_1$, the signal $s_3$ drops to a low state for a short time, as indicated at 80 of FIG. 5A, so as to cause the output of the AND gate 74 and hence the D input of the latch $L_{12}$ to have a zero value. While the signal $s_3$ is at the low state 80, a short pulse 81 appears in the signal $s_4$ so as to trigger the latch $L_{12}$ and transfer the zero value from its D input to its Q output and to the input 76 of the adder 72, thereby making the circuit ready to add the next group of data samples as just described. Before $L_{12}$ is set to zero, a narrow pulse 82 in the signal $s_5$ causes the latch $L_{13}$ to transfer the average value of the samples of the group to its Q output, where it will remain while data samples of the next group arrive and until the next narrow pulse 82 of the signal $s_5$ occurs.

The means for deriving the absolute value of the difference between each data sample of a group and the average value of the data samples of the previous group is comprised of a subtractor 84 and an absolute value circuit 86 connected to the output of the subtractor 84. One input of the subtractor 84 is connected to the Q output of the latch $L_{10}$ so as to receive the data samples of the new group as they arrive, and the other input is connected to the Q output of the latch $L_{13}$ so as to receive the average value of the data samples of the previous group. The output of the subtractor 84 thus successively represents the difference between each data sample and the average value of the previous group of data samples, and the absolute value of the difference is provided by an absolute value circuit 86.

The following means are used for identifying the data sample of one group that differs the most from the average value of the data samples of a previous group and for conducting it to an output 88 that is connected to a display means 90. The output of the absolute value circuit 86 is applied to an input 92 of an AND gate 94 as well as to the Y input of a comparator 96. Only one AND gate 94 is shown, but there would be as many as there are data lines. The signal $s_3$ is applied to the other input 98 of the AND gate 94, and the output of the AND gate 94 is connected to the D input of a latch $L_{14}$. The Q output of the latch $L_{14}$ is connected to the X input of the comparator 96. The comparator 96 produces a high state on its output lead 100 if the signal at its X input represents a value less than the value represented by the signal at its Y input. The output lead 100 is connected to the D input of a latch $L_{15}$, and the Q output of $L_{15}$ is connected to one input of an OR gate 102. A signal $s_2$ is coupled to the trigger input of $L_{15}$. A signal $s_6$ having a pulse 103 that is opposite in polarity to the pulse 80 of the signal $s_3$ is applied to the other input of the OR gate 102. The output of the OR gate 102 is applied to one input of an AND gate 104, and the signal $s_4$ is applied to the other input. The output of the AND gate 104 is connected to the trigger input of the latch $L_{14}$, which has its D input connected to the output of the AND gate 94 and its Q output connected to the X input of the comparator 96. The output of the AND gate 104 is also connected to the trigger input of a latch $L_{16}$ having its D input connected to the Q output of the latch $L_{10}$, and its Q output connected to the D input of a latch $L_{17}$. The Q output of the latch $L_{17}$ is connected to the lead 88, and the latch $L_{17}$ is triggered by the signal $s_5$.

The manner in which the portion of the circuit just described operates to select the data sample that is to be the display sample of a group is as follows. Assume that the Q output of the latch $L_{14}$ and thus the X input of the comparator 96 have been set to zero in a manner to be described. When the first data sample causing an absolute value that is other than zero arrives at the Y input of the comparator 96, the outputlead 100 acquires a high state so that the Q output of the latch $L_{15}$ can be triggered high when a pulse such as 77 of signal $s_2$ arrives shortly thereafter. Because the signal $s_6$ is low when pulse 77 occurs, the output of the OR gate 102 goes high as does the input of the AND gate 104 to which it is connected. Thus, when a high state pulse such as 78 from signal $s_4$ occurs, both inputs of the AND gate 104 are high, and its output goes high so as to trigger the latch $L_{14}$. Prior to the time when the latch $L_{14}$ is triggered, the absolute value at the output of the circuit 96 is present at the D input of the latch $L_{14}$ because the high state of the signal $s_3$ allows it to pass through the AND gate 94. Therefore, when the latch $L_{14}$ is triggered, the absolute value that caused it is transferred to the X input of the comparator 96 where it is compared with the absolute value caused by the next data sample. If the latter absolute value is greater than the previous one, the latch $L_{14}$ is triggered; but if it is not greater, nothing happens. The latch $L_{16}$ is also triggered by the AND gate 104 so that it transfers the data sample corresponding to a larger absolute value from its D input to its Q output and to the D input of the latch $L_{17}$. After the absolute values of all data samples of a group have been compared, the data sample that differs the most from the average value of the preceding group of data samples will be at the D input of the latch $L_{17}$. When the latch $L_{17}$ is triggered by the pulse 82 of the signal $s_5$, the data sample is passed via the lead 88 to the display means 90.

Resetting the X input of the comparator 96 to zero so as to be ready for the next group of data samples is done as follows. After the last pulse 79 of the group in the signal $s_1$ has caused the last data sample of a group to appear at the Q output of $L_{10}$, the signal $s_3$ drops to a low state as indicated at 80 so as to cause the output of the AND gate 94 and the D input of the latch $L_{14}$ to have a low state or zero value. This low state is transferred to the X input of the comparator 96 by triggering the latch $L_{14}$. Because the output of the latch $L_{15}$ to which one input of the OR gate 102 is connected may or may not be high, a high state pulse 103 of the signal $s_6$ is applied to the other input of the OR gate 102 so as to ensure that its output will be high. Then when a pulse 81 of the signal $s_4$ occurs, both inputs of the AND gate 104 are high so as to cause its output to go high and thereby trigger the latch $L_{14}$ as required.

Preferred Embodiment for Performing the First Invented Procedure

Figure 6:
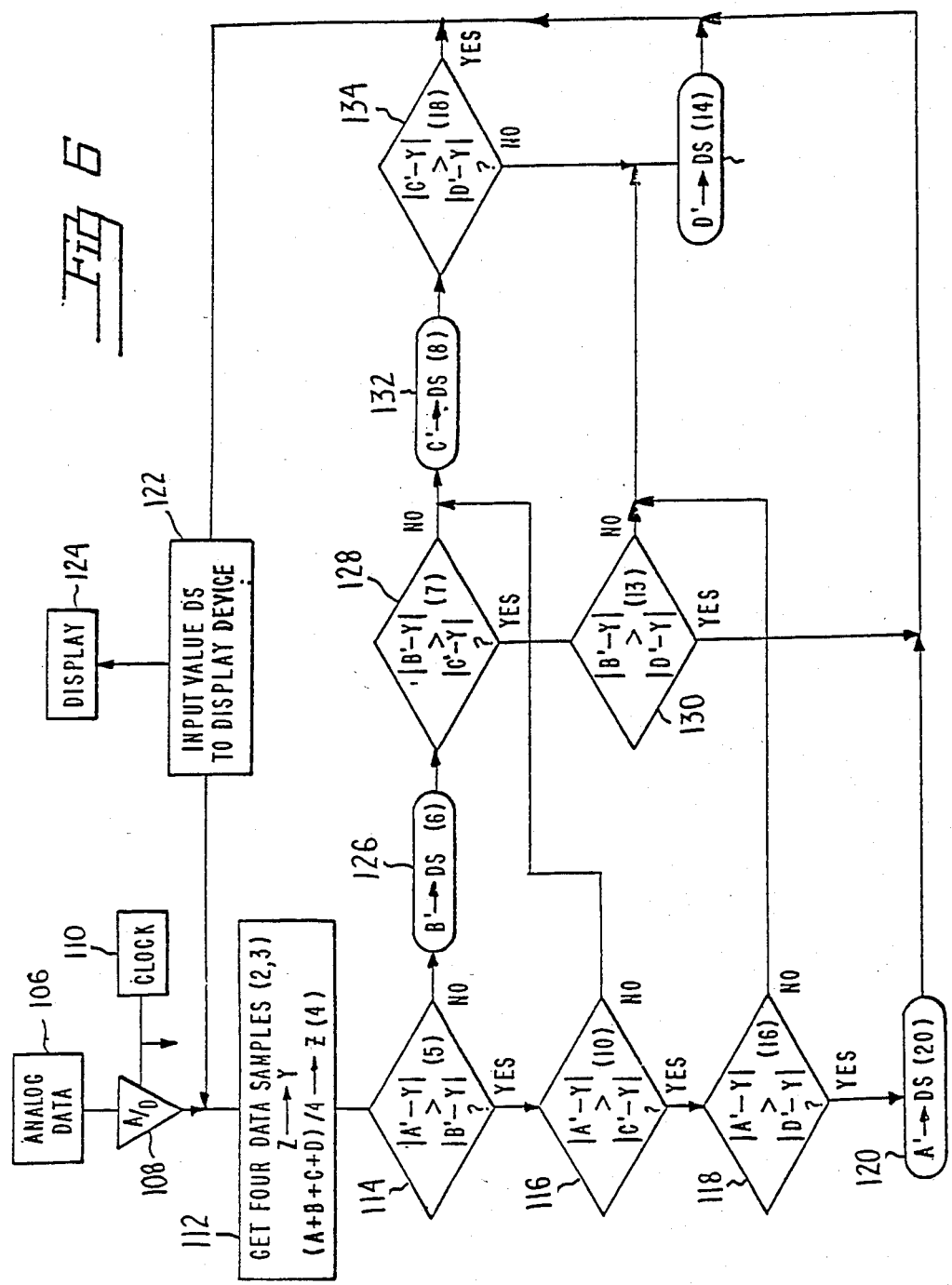
FIG. 6 is a flow chart illustrating one way in which the data sample that is to be the display sample may be selected by a processor or computer in accordance with the first invented procedure.

Whereas the first invented procedure can be performed with the circuits of FIG. 4 or 5 in the manner described, it is generally preferable to utilize a microprocessor or computer, especially if they are available for other purposes. FIG. 6 illustrates a flow chart that can be used as a basis for formulating programs for any general purpose processor or computer, but the program set forth below is for the Hewlett-Packard HP-9825A programmable calculator. The numerals within the blocks of the flow chart are the numbers of the related steps in the program.

Analog data is provided by a source 106 to an A/D converter 108 that is timed by a system clock 110. During the occurrence of a first group of data samples A, B, C and D, the program (steps 2, 3 and 4 of block 112) places the average of the previous four samples Z in Y and calculates a new average Z to be used with the next group of samples A', B', C' and D'. In this way, Y always contains the average of the previous four samples. The data sample of a second group A', B', C' and D' that is a possible display sample at various points in the program is placed in a register DS, not shown. Decision blocks 114, 116 and 118 respectively determine if $|A'-Y| > |B'-Y|$, if $|A'-Y| > |C'-Y|$, and if $|A'-Y| > |D'-Y|$. The program progresses from one block to the next only if the answer is affirmative. If all decisions are affirmative, data sample A' is put in the display register DS, block 120, and as indicated at block 122, it is output to a display means 124. If the answer in block 114 is negative, then B' is a possible display sample and is put in the register DS, block 126, until a final determination is made. But before B' is designated as a display sample, blocks 128 and 130, which respectively determine if $|B'-Y| > |C'-Y|$ and if $|B'-Y| > |D'-Y|$, must yield affirmative answers. If they do, data sample B' which is already in the register DS is inputted to the display device 124 as indicated at block 122. If, however, the decision of the block 128 is negative, data sample C' now becomes a possible display sample and is placed in the register DS, block 132, but before being designated as the display sample, a block 134 must produce an affirmative answer indicating that $|C'-Y| > |D'-Y|$. If the answer of the block 134 is affirmative, the data sample C' which is already in the register DS is inputted to the display device 124 as indicated at block 122. If the decision of either of the blocks 130 or 134 is negative, then the data sample D' is placed in the DS register, block 136, and inasmuch as the process is completed, the sample D' is inputted to the display device 124 as indicated at block 122.

If the decision of the block 114 is affirmative, i.e., $|A'-Y| > |B'-Y|$, but the decision of the block 116 is negative, i.e., $|A'-Y| < |C'-Y|$, then data sample C' may be the display sample and is put into the DS register, block 132. The program then continues from the block 132 to determine whether $|C'-Y| > |D'-Y|$, block 134, as before. If so, data sample C' is inputted to the display device 122 from the register DS; but if not, data sample D' is the display sample and it is placed in the register DS, block 136. From there, the data sample D' is inputted to the display device 124, block 122. If the answers of the blocks 114 and 116 are both affirmative and the decision of the block 118 is negative, i.e., $|A'-Y| < |D'-Y|$, then data sample D' is the display sample and is placed in the register DS, block 136. From there it is transferred, block 122, to the display device 124.

Program for HP-9825A for the First Invented Procedure

0: "enhl":dsp "in enhl"
1: for I=1 to 8192 by 8
2: itf(K$[I,I+1])→r1; itf(K$[I+2,I+3])→r2
3: itf(K$[I+4,I+5])→r3; itf(K$[I+6,I+7])→r4
4: Z→Y; (r1+r2+r3+r4)/4→Z
5: if abs(r1−Y) abs(r2−Y); gto 10
6: r2→C
7: if abs(r2−Y)>abs(r3−Y); gto 13
8: r3→C
9: gto 18
10: if abs(r1−Y)>abs(r3−Y); gto 16
11: r3→C
12: gto 18
13: if abs(r2−Y)>abs(r4−Y); gto 21
14: r4→C
15: gto 21
16: if abs(r1−Y)>abs(r4−Y); gto 20
17: gto 14
18: if abs(r3−Y) abs(r4−Y); gto 21
19: gto 14
20: r1 C
21: dsp C
22: next I.

Results Attained

Figure 7:
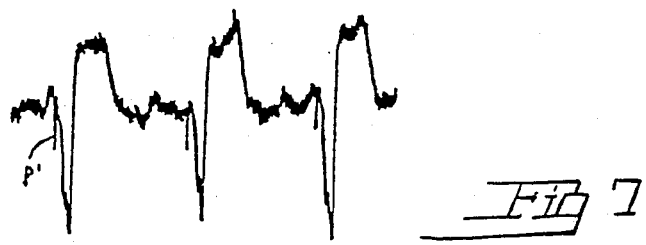
FIG. 7 illustrates an ECG wave formed from actual data samples.
Figure 8:
FIG. 8 illustrates an ECG wave formed by using the average values of each group of four actual data samples.
Figure 9:
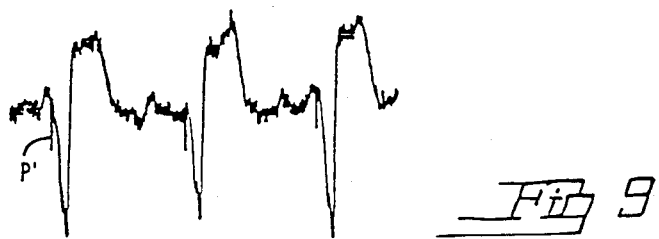
FIG. 9 illustrates an ECG wave formed by selecting a data sample of each group of four as a display sample in accordance with the first invented procedure.

FIG. 7 illustrates an ECG wave formed by using all data samples which occur every 2 milliseconds as display samples; FIG. 8 illustrates the same ECG wave formed by using the average of each successive and exclusive group of four data samples as a display sample; and FIG. 9 illustrates the same ECG wave formed by selecting one data sample in each successive and exclusive group of four data samples in accordance with the first procedure of this invention. Note that the pace pulse P′ of FIG. 7 is completely lost in the noise in the ECG wave of FIG. 8, but that it retains its full amplitude in the ECG wave of FIG. 9. This is of significance when evaluating the performance of a pacemaker device in a patient.

Comment

In the embodiments thus far described for carrying out the first invented procedure, one data sample in four is selected as a display sample. Whereas this would seem to indicate a severe reduction in information content, as actually occurs in the averaging method of data compression illustrated in FIG. 8, it has been found that the loss in information content is considerably reduced using the described technique. The invention may be applied by using groups containing two or more data samples, but if the number of data samples in a group is not a power of 2, the average of the data samples in a group must be determined by a true divider rather than by eliminating bits of lower significance. The loss in information content will, of course, increase as the number of samples in a group is increased. It is thought that the circuits as well as the program could be altered by one skilled in the art to work with groups having other than four data samples. It will also be appreciated that the particular decisions illustrated in the flow chart of FIG. 6 could be altered as long as a final determination is made as to which data sample of a group differs the most from the average of the data samples of the previous group.

Another Procedure Incorporating the Invention

Figure 10:
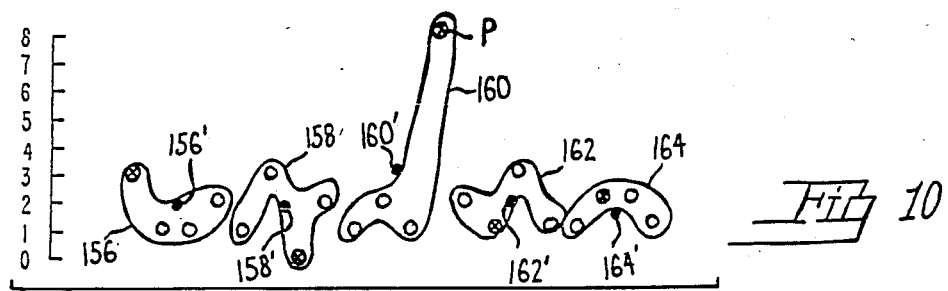
FIG. 10 is the same as FIG. 1.
Figure 11:
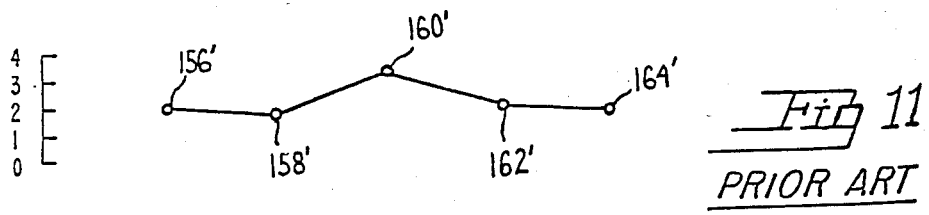
FIG. 11 is the same as FIG. 2.

In FIG. 10, each data sample is indicated by an "O", successive groups of four data samples are respectively encircled by separate lines 156, 158, 160, 162 and 164, and the average of the data samples in each group are indicated by points 156′, 158′, 160′, 162′ and 164′ respectively. The data point P in the group 160 represents a pace pulse. FIG. 11 illustrates the electrocardiogram which would result if the data is compressed by using the average values 156′, 158′, 160′, 162′ and 164′ of each group of data samples. Note that the pace pulse P represented by the display sample 160′ of the group 160 is greatly attenuated.

Figure 12:
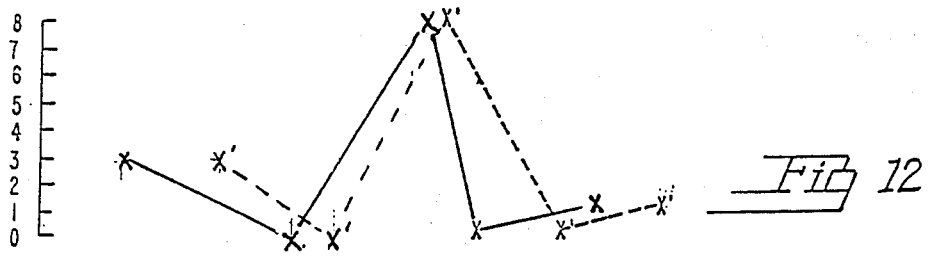
FIG. 12 illustrates the data samples of each group of FIG. 10 that are selected as display samples in accordance with a second invented procedure.

In accordance with a second invented procedure, the data sample in each of the groups 156, 158, 160, 162 and 164 that is selected as a display sample is the data sample that differs from the data sample selected from the previous group by the greatest absolute amount. In FIG. 10, the data samples that are selected as display samples are indicated by an "X" and are separately plotted and joined by a solid line in FIG. 12. It can be seen that the pace pulse P is selected as a display sample. In view of the fact that the data sample of a group that is to be selected as a display sample cannot be determined until all data samples of the group have been examined, the data sample of a group that has been selected as a display sample is supplied to the display means at a point between the last data sample of the group and the first data sample of the next group, as indicated by the X's in FIG. 12 that are connected by a dashed line.

Figure 13A:
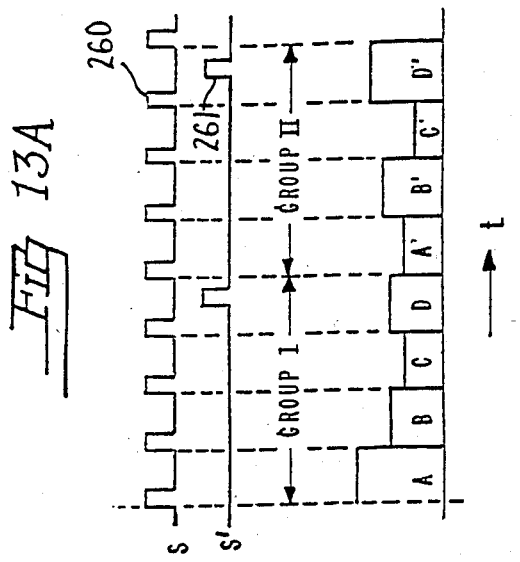
FIG. 13A illustrates input and output strobing pulses used in FIG. 13, as well as data samples used in the explanation of the operation of FIG. 13.
Figure 13:
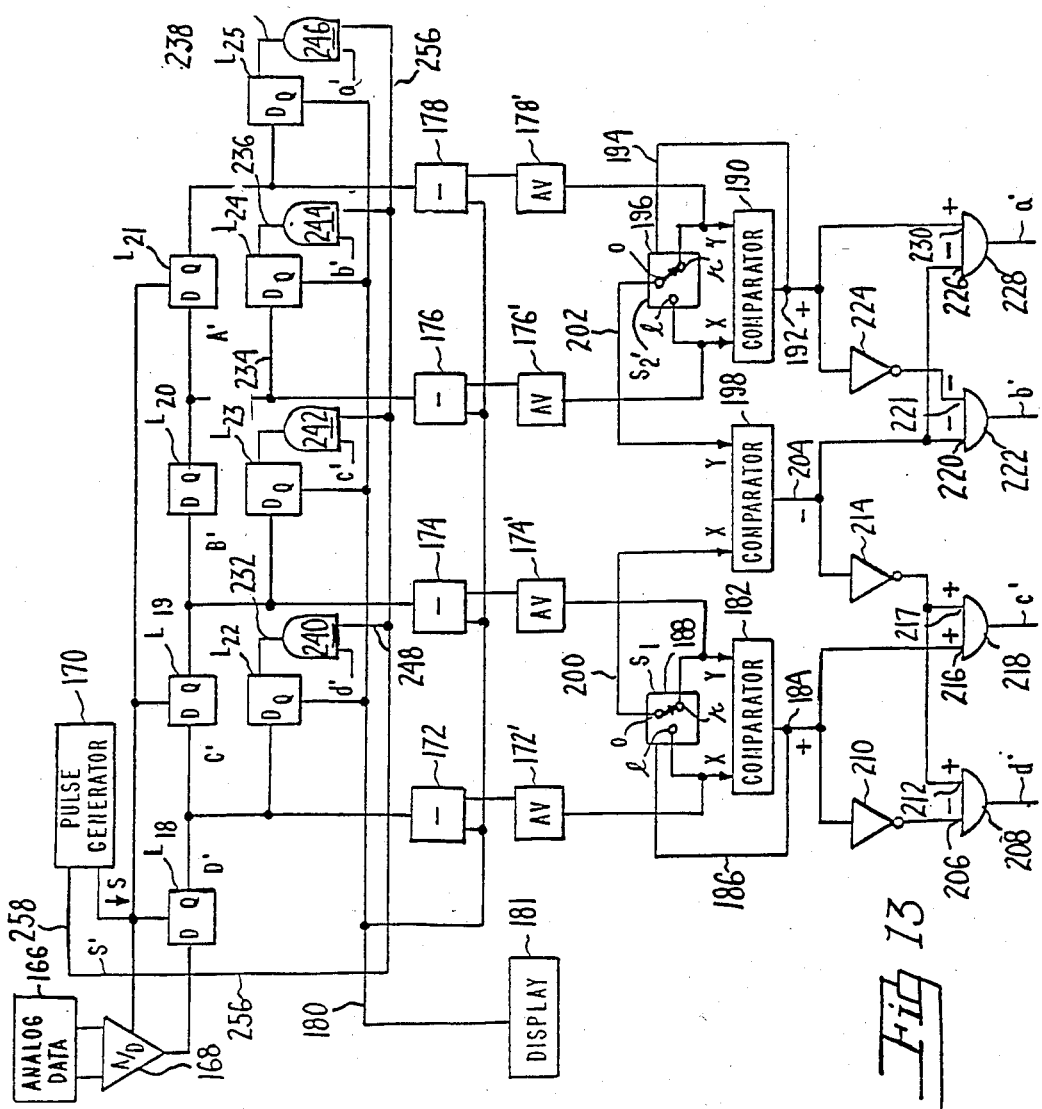
FIG. 13 is a block diagram of a circuit for selecting the data sample of each group that is to be a display sample in accordance with the second invented procedure in which the absolute differences between all data samples of a group and the data sample selected from the previous group are made simultaneously available before the data sample having the largest absolute difference is selected as the display sample.

Reference is now made to the circuit of FIG. 13 that selects the data samples that are to be the display samples in accordance with the second invented procedure. Analog data, such as the output of an ECG machine, is supplied by a source 166 to an A/D converter 168 that supplies digitized data samples to a latch $L_{18}$ that is connected in series with latches $L_{19}$, $L_{20}$ and $L_{21}$. The Q output of each latch is connected to the D input of the next latch in the series so as to form a shift register. The A/D converter 168 and the latches $L_{18}$, $L_{19}$, $L_{20}$ and $L_{21}$ are simultaneously strobed by pulses S illustrated in FIG. 13A that are supplied by a pulse generator 170. Any form of digital counter may be used, but a Johnson counter is satisfactory. The Q outputs of the latches $L_{18}$, $L_{19}$, $L_{20}$ and $L_{21}$ are respectively connected to the D inputs of latches $L_{22}$, $L_{23}$, $L_{24}$ and $L_{25}$ as well as to inputs of subtracting means 172, 174, 176 and 178. The other inputs of the subtracting means 172, 174, 176 and 178 are connected to a data output bus 180 so as to receive the data sample of the previous group that was selected as a display sample. The output bus 180 is connected to a display means 181. The outputs of the subtracting means 172, 174, 176 and 178 are respectively connected to absolute value circuits 172′, 174′, 176′ and 178′. The outputs of the absolute value circuits 172′ and 174′ are respectively connected to the X and Y inputs of a comparator 182 as well as to input terminals l and r of a switch $S_1'$. When the value at its input X is less than the value at its input Y, the comparator 182 produces a high state at its output 184. The output 184 is connected via a lead 186 to a control terminal 188 of the switch $S_1'$. When the control terminal 188 is in a high state, the output O of the switch is connected to its input terminal r.

The outputs of the absolute value circuits 176′ and 178′ are respectively connected to inputs X and Y of a comparator 190 as well as to input terminals l and r of a switch $S_2'$. When the value of the input X is less than the value at the input Y, the comparator 190 produces a high state at an output 192. The output 192 is connected via a lead 194 to a control terminal 196 of the switch $S_2'$. When the control terminal 196 is in a high state, the output O of the switch $S_2'$ is connected to its input terminal r.

The outputs O of the switches $S_1'$ and $S_2'$ are respectively connected to the X and Y inputs of a comparator 198 via leads 200 and 202. When a value at its input X is less than the value at its input Y, the comparator 198 produces a high state at its output 204.

The means for selecting the data sample having the greatest absolute difference from the data sample of the previous group of data samples may include the following logic circuits. An input 206 of an AND gate 208 is connected via an inverter 210 to the output 184 of the comparator 182, and its other input 212 is connected via an inverter 214 to the output 204 of the comparator 198. An input 216 of an AND gate 218 is connected to the output 184 of the comparator 182, and its other input 217 is connected via the inverter 214 to the output 204 of the comparator 198. An input 220 of an AND gate 222 is connected to the output 204 of the comparator 198, and its other input 221 is connected via an inverter 224 to the output 192 of the comparator 190. An input 226 of an AND gate 228 is connected to the output 204 of the comparator 198, and its other input 230 is connected to the output 192 of the comparator 190.

The conduction of the selected data sample of a group to the output bus 180 and thus to the display means 181 is accomplished as follows. The respective outputs 232, 234, 236 and 238 of AND gates 240, 242, 244 and 246 are respectively connected to the trigger inputs of the latches $L_{22}$, $L_{23}$, $L_{24}$ and $L_{25}$. The inputs 248, 250, 252 and 254 of the AND gates 240, 242, 244 and 246 respectively are connected via a bus 256 to an output 258 of the pulse generator 170 at which the output strobing pulses S' of FIG. 13A appear and, although not shown, the respective inputs d', c', b' and a' of the AND gates 240, 242, 244 and 246 are respectively connected to the outputs d', c', b' and a' of the AND gates 208, 218, 222 and 228. In a manner to be explained, only one of the outputs d', c', b' and a' will be in a high state when an output strobing pulse S' appears on the bus 256 so that only one of the AND gates 240, 242, 244 and 246 will have both inputs in a high state so as to cause its output to have a high state. The latch $L_{22}$, $L_{23}$, $L_{24}$ or $L_{25}$ to which that output is connected will be triggered so as to transfer the data sample at its D input to its Q output and thus to the data sample output bus 180 and the display means 181. The data sample will remain at these points until the strobing pulse S' of the next group of data samples occurs, at which point a new data sample will be conducted to the bus 180.

Operation of FIG. 13

The overall operation of the circuit of FIG. 13 will now be explained by reference to the signals S and S' of FIG. 13A as well as to data sample values, A, B, C and D of group I and A', B', C' and D' of group II. Assume that the data sample A of group I was selected as the display sample for that group. After the fourth pulse 260 of the input strobing signal S has occurred, the values of the data samples A', B', C' and D' will be at the Q outputs of the latches $L_{21}$, $L_{20}$, $L_{19}$ and $L_{18}$ respectively, as indicated. This seeming inversion results from the fact that the data sample A' is the first one of group II to be received so that it advances through all the latches $L_{18}$, $L_{19}$, $L_{20}$ and $L_{21}$ in sequence. The outputs of the subtractors 172, 174, 176 an 178 will be D'−A, C'−A, B'−A and A'−A respectively and the outputs of the absolute value circuits 172', 174', 176' and 178' will be $|D'-A|$, $|C'-A|$, $|B'-A|$ and $|A'-A|$ respectively. By inspection, it can be seen that $|C'-A| > |D'-A|$ so that the output 184 of the comparator 182 will be in a high state (+) and cause the output O of the switch $S_1'$ to be connected to its input terminal r as schematically indicated by the arrow, thereby supplying the value $|C'-A|$ to the X input of the comparator 198. It can also be seen that $|A'-A| > |B'-A|$ so that the output 192 of the comparator 190 will be in a high state (+) and cause the output O of the switch $S_2$ to be connected to its input terminal r as schematically indicated by the arrow, thereby supplying the value $|A'-A|$ to the Y input of the comparator 198. Inasmuch as $|C'-A| > |A'-A|$, the output 204 of the comparator 198 will be in a low state (−). Examination of the resulting states at the inputs of the AND gates 208, 218, 222 and 228 shows that the AND gate 218 is the only one having both inputs in a high state so that its output c' is the only one in a high state. Thus, when the output strobing pulse 261 of the group II occurs, the output of the AND gate 242 will go to a high state and trigger the latch $L_{23}$. The latch $L_{23}$ then transfers the value of the data sample C' to its Q output and the data sample output bus 180 where it will remain until the next pulse of the signal S' occurs.

Alternative Circuit

The circuit of FIG. 14 examines each data sample of a current group in sequence to determine whether its absolute difference from the display sample of the previous group is greater than the absolute difference due to previous data samples in the current group. If so, it is temporarily stored in a latch, and when all current data samples have been examined, the data sample then in the latch is transferred to a display means. An analog data source 264, e.g., an ECG machine, is connected to an A/D converter 266 that supplies digitized samples of the analog data to the D input of a latch $L_{26}$. Its Q output is connected to the D input of a latch $L_{27}$ and to one input 268 of a subtractor 270. The Q output of the latch $L_{27}$ is connected to the D input of a latch $L_{28}$ and its Q output is connected to the other input 272 of the subtractor 270 as well as to a display means 274.

An output 276 of the subtractor 270 is connected to an absolute value circuit 278, and its output 279 is connected to one input 280 of an AND gate 282. In the interest of simplicity, only one data line has been shown, but any number could be used. The number of AND gates 282 would equal the number of data lines. The output 284 of the AND gate 282 is connected to the D input of a latch $L_{29}$, and the Q output of the latch $L_{29}$ is connected to the X input of a comparator 286. The Y input of the comparator 286 is connected to the output 279 of the absolute value circuit 278. The output 288 of the comparator 286 has a high state only if the value of its X input is less than the value at its Y input and is connected to the D input of a latch $L_{30}$. The Q output 290 of the latch $L_{30}$ is connected to one input of an OR gate 292. One input 294 of an AND gate 296 is connected to the output of the OR gate 292, and the output 300 of the AND gate 296 is connected to the trigger input of the latch $L_{29}$ as well as to the trigger input of the latch $L_{27}$.

A signal generator 302 supplies the signals $s_1$, $s_2$, $s_3$, $s_4$, $s_5$ and $s_6$ shown in FIG. 14A to the indicated points in the circuit: the signal $s_1$ being supplied to the trigger inputs of the A/D converter 266 and the latch $L_{26}$; the signal $s_2$ being supplied to the other input 304 of the AND gate 282; the signal $s_3$ being supplied to the other input 306 of the AND gate 296; the signal $s_4$ being supplied to the trigger input of the latch $L_{28}$; the signal $s_5$ being supplied to the other input 308 of the OR gate 292; and the signal $s_6$ being supplied to the trigger input of the latch $L_{29}$. One skilled in the art could provide these signals with a Johnson counter, OR gates and astable multivibrators.

Each pulse of the signal $s_1$ causes a different data sample to appear at the Q output of the latch $L_{26}$ and the D input of the latch $L_{27}$. Assume that the data samples in FIG. 14A arrive in the sequence A', B', C' and D' and that the display sample that was selected from the previous group of data samples is DS. Also assume that the X input of the comparator 286 has been set to zero value before the first data sample A' arrives in response to the first pulse 309 of the signal $s_1$. During the data sample A', the output of the subtractor 270 is A'−DS and the output of the absolute value circuit 276 that is applied to the Y input of the comparator 286 is $|A'-DS|$. Owing to the fact that the signal $s_2$ at the input 304 of the AND gate 282 is high, the value A'−DS passes to the D input of the latch $L_{29}$, but its Q output and therefore the X input of the comparator 286 remain at zero value. Inasmuch as this is less than the value $|A'-DS|$ applied to the Y input of the comparator 286, its output has a high state. This high state appears at the D input of the latch $L_{30}$ until the first pulse 324 of the signal $s_6$ advances it to the Q output. It then passes through the OR gate 292 to the input 294 of the AND gate 296 and, when the first pulse 310 of the signal $s_3$ arrives at the other input 306 of the AND gate 296, its output goes high so as to trigger the latch $L_{29}$ and transfer the value $|A'-DS|$ to the Q output of the latch and the X input of the comparator 286. The second pulse 312 of the signal $s_1$ causes the data sample B' to appear at the input 268 of the subtractor 270, but by inspection it can be seen that $|A'-DS|>|B'-DS|$ so that the output 288 of the comparator 286 drops to a low state and the value $|A'-DS|$ remains at the X input of the comparator. However, when the data sample C' arrives, $|C'-DS|>|A'-DS|$ so that the output 288 of the comparator 286 is high, thereby triggering the latches $L_{29}$ and $L_{30}$ as described previously and placing the value $|C'-DS|$ at the X input of the comparator. Inasmuch as $|D'-DS|<|C'-DS|$, the latches $L_{30}$ and $L_{29}$ are not triggered when D' arrives.

Each time the latch $L_{29}$ is triggered, the latch $L_{27}$ is triggered so that the data sample A' was transferred to the Q output of the latch $L_{27}$. Since the latches were not triggered in response to the data sample B', the data sample A' remained at the Q output of the latch $L_{27}$, but when the data sample C' arrived, the latches $L_{27}$ and $L_{29}$ were triggered with the result that the data sample C' took the place of the data sample A'. As the latches were not triggered in response to the data sample D', the data sample C' was not removed.

The X input of the comparator 286 is set to a zero value in preparation for the next group of samples as follows. After the last data sample D' in the group has arrived and after the last pulse 314 of the signal $s_3$, the value at the Q output of the latch $L_{27}$ is C'; but if the data sample D' differed more from DS than C', there would be enough time for D' to reach the Q output of the latch $L_{27}$. After enough time for this to occur, the signal $s_2$ drops to a low state, as indicated at 316, so as to cause the output of the AND gate 282 and the D input of the latch $L_{29}$ to drop to a low state or zero value. When a narrow pulse 318 of the signal $s_3$ arrives at the input 306 of the AND gate 296, its output 300 will go high and trigger the latch $L_{29}$ so as to transfer the zero value at its D input to its Q output and thus to the X input of the comparator 286 if the other input 306 of the AND gate 296 is also at a high state. As this may or may not be the case, depending on the effect of the sample D', a pulse 320 of the signal $s_5$ is applied to the input 308 of the OR gate 292. Thus, regardless of the effect of the sample D', the input 294 of the AND gate 296 will be high when the pulse 218 makes its other input 306 high so that the latch $L_{29}$ is triggered. The zero value at the D input of the latch $L_{29}$ is transferred to its Q output and therefore to the X input of the comparator 286. The circuit is now ready to analyze the next group of data samples.

The data sample C' that is at the D input of the latch $L_{28}$ is transferred to the display means 279 by application of the pulse 325 of the signal $s_4$ to the trigger input of the latch $L_{28}$. The pulse 325 occurs before the pulse 318 so as to transfer the selected data sample, in this example C', to the display means 274 before the clearing of latch $L_{29}$ and the simultaneous strobing of S' into $L_{27}$ by the pulse 318.

Preferred Embodiment for Performing the Second Invented Procedure

Whereas the second invented procedure can be performed with the circuits of FIGS. 13 and 14 in the manner described, it is generally preferable to utilize a microprocessor or computer, especially if they are available for other purposes. FIG. 15 illustrates a flow chart that can be used as a basis for formulating programs for any general purpose processor or computer, but the program set forth below is for the Hewlett-Packard HP-9825A programmable calculator. The numerals within the blocks are the numbers of the related steps in the program.

Analog data is provided by a source 326 to an A/D coverter 327 that is timed by a system clock 328 which controls the rate at which the various steps of the program proceed. During the occurrence of a first group of data samples A, B, C and D, the program steps 2, 3 and 4 of block 329 place the value of the data sample of the previous group that was selected as the display sample for that group into the Y register, not shown, where it can be used during the processing of the next group of samples A', B', C' and D' that is now described. The data sample of the group A', B', C' and D' that is a possible display sample at various points in the program is placed in a register DS, not shown. Decision blocks 330, 332 and 334 respectively determine if $|A'-Y|>|B'-Y|$, if $|A'-Y|>|C'-Y|$, and if $|A'-Y|>|D'-Y|$. The program progresses from one block to the next only if the answer is affirmative. If all these decisions are affirmative, data sample A' is put in the display register DS, block 336, and as indicated at block 338, it is output to a display means 340. If the answer in block 330 is negative, then B' is a possible display sample and is put in the register DS, block 342, until a final determination is made. But before B' is designated as a display sample, blocks 344 and 346 which respectively determine if $|B'-Y|>|C'-Y|$ and if $|B'-Y|>|D'-Y|$ must yield affirmative answers. If they do, data sample B' which is already in the register DS is inputted to the display device 340 as indicated at block 338. If, however, the decision of the block 344 is negative, data sample C' now becomes a possible display sample and is placed in the register DS, block 348, but before being designated as the display sample, a block 350 must produce an affirmative answer indicating that $|C'-Y|>|D'-Y|$. If the answer of the block 350 is affirmative, the data sample C' which is already in the register DS is inputted to the display device 340 as indicated at block 338. If the decision of block 350 is negative, then the data sample D' is placed in the DS register, block 352, and inasmuch as the process is completed, the sample D' is inputted to the display device 340 as indicated at block 338.

If the decision of the block 330 is affirmative, i.e., $|A'-Y|>|B'-Y|$, but the decision of the block 332 is negative, i.e., $|A'-Y|<|C'-Y|$, then data sample C' may be the display sample and is put into the DS register as indicated in block 348. The program then continues from block 348 to determine whether $|C'-Y|>|D'-Y|$, block 350, as before. If so, data sample C' is inputted to the display device 340 from the register DS; but if not, data sample D' is the display sample and it is placed in the register DS, block 352. From there, the data sample D' is inputted to the display device 340, block 338. If the answers of the blocks 330 and 332 are both affirmative and the decision of the block 334 is negative, i.e., $|A'-Y|<|D'-Y|$, then data sample D' is the display sample and is placed in the register DS, block 352. From there, it is transferred, block 338, to the display device 340.

It will be appreciated that the particular decisions illustrated in the flow chart of FIG. 15 could be altered as long as a final determination is made as to which data sample of a group differs the most from the previous sample.

Program for HP-9825A for the Second Invented Procedure

0: "enhl":dsp "in enhl"
1: for I=1 to 8192 by 8
2: itf(K$[I,I+1])→r1; itf(K$[I+2,I+3])→r2
3: itf(K$[I+4,I+5])→r3; itf(K$[I+6,I+7])→r4
4: C→Y
5: if abs(r1−Y)>abs(r2−Y); gto 10
6: r2→C
7: if abs(r2−Y)>abs(r3−Y); gto 13
8: r3→C
9: gto 18
10: if abs(r1−Y)>abs(r3−Y); gto 16
11: r3→C
12: gto 18
13: if abs(r2−Y)>abs(r4−Y); gto 21
14: r4→C
15: gto 21
16: if abs(r1−Y)>abs(r4−Y); gto 20
17: gto 14
18: if abs(r3−Y)>abs(r4−Y); gto 21
19: gto 14
20: r1→C
21: dsp C
22: next I.

Results Attained

Figure 16:
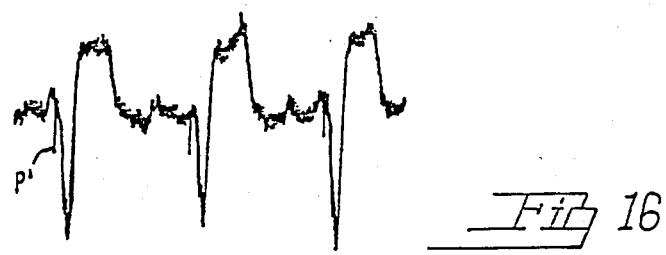
FIG. 16 is an ECG wave formed from some actual data samples.
Figure 17:
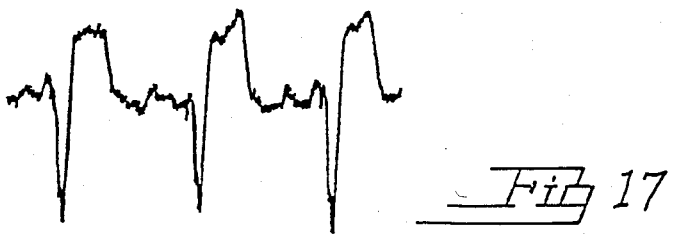
FIG. 17 is an ECG wave formed from display samples selected by averaging the groups of the data samples used in forming the ECG wave of FIG. 16.
Figure 18:
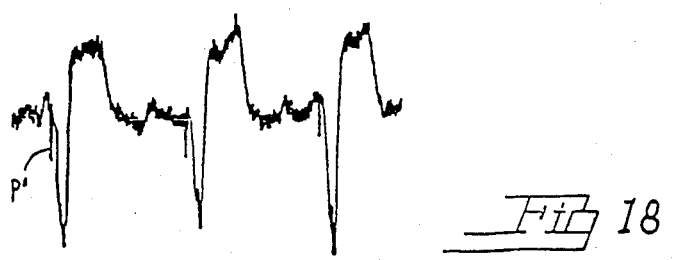
FIG. 18 is an ECG wave formed by selecting a display sample from each group of four data samples in accordance with the second invented procedure.

FIG. 16 illustrates an ECG wave formed by using all original data samples occurring every two milliseconds as display samples. FIG. 17 illustrates an ECG wave formed from the same original data samples by using the average of each consecutive group of four as a display sample. FIG. 18 illustrates an ECG wave formed in accordance with this invention from the same original data samples by selecting as the display sample those data samples in each consecutive group of four having the greatest absolute difference with respect to the data sample selected as the display sample for the previous group. Note that the pace pulse P' of FIG. 16 is completely lost in the noise in the ECG wave of FIG. 17, but that it retains its full amplitude in the ECG wave of FIG. 18. This is of significance when implanting or evaluating the performance of a pacemaker device in a patient.

What is claimed is:

1. Apparatus for compressing data represented by samples occurring at a given frequency in such manner that it can be displayed with a minimum of loss of significant detail, comprising an input means to which said samples representing successive values of data can be applied,
an output means,
means coupled to said input means for deriving a representation of an average of the values represented by each successive group of data samples,
means for providing a signal identifying the data sample of each group having the greatest absolute difference with respect to the average of the data samples of the previous group,
means responsive to said signal for conducting the data sample having the said greatest absolute difference to said output means,
a display means, and
means for coupling said output means to said display means.

2. A method for compressing sampled data comprising determining the average amplitude of a group of a given number of samples,
storing the average so obtained,
determining the absolute value of the difference between each sample of a following group of samples of like number and the stored average, and
supplying the sample of the latter group having the largest absolute difference to an output means.

3. Apparatus for compressing data represented by a series of samples, comprising a shift register having a plurality of sections,
means for consecutively loading each sample of a first group of samples into one end of said shift register,
means for deriving the average of the amplitudes of the first group of samples that are respectively in said sections,
means for temporarily storing the average value,
means for consecutively loading each sample of a current group of samples into the said one end of said shift register,
means for deriving the absolute value of the difference between the said temporarily stored average value and each sample of the current group of samples respectively stored in each of said sections,
means for determining the section having the sample with the largest absolute value, and
means for applying the sample in said latter section to an output means.

4. Apparatus for compressing data represented by a series of samples, comprising an input means to which samples can be applied in sequence,
means coupled to said input means for deriving the average amplitude of each successive group of samples,
means for deriving the absolute value of the difference between the amplitude of each sample of a current group of samples and the average amplitude of the previous group of samples,
means for determining the sample of the current group producing the largest absolute value, and
means for supplying the latter sample to an output means.

* * * * *